United States Patent
Tanida

(10) Patent No.: US 11,594,299 B2
(45) Date of Patent: Feb. 28, 2023

(54) METHOD FOR SEARCHING FOR MODIFICATION SITE OF PEPTIDE MOLECULE AND INFORMATION PROCESSING APPARATUS

(71) Applicant: FUJITSU LIMITED, Kawasaki (JP)

(72) Inventor: Yoshiaki Tanida, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 390 days.

(21) Appl. No.: 17/001,020

(22) Filed: Aug. 24, 2020

(65) Prior Publication Data

US 2021/0118523 A1   Apr. 22, 2021

(30) Foreign Application Priority Data

Oct. 21, 2019   (JP) .............................. JP2019-191785

(51) Int. Cl.
*G16B 15/30*   (2019.01)
*G16B 45/00*   (2019.01)
*G06F 30/20*   (2020.01)
*G06F 111/10*  (2020.01)

(52) U.S. Cl.
CPC ............. *G16B 15/30* (2019.02); *G06F 30/20* (2020.01); *G16B 45/00* (2019.02); *G06F 2111/10* (2020.01)

(58) Field of Classification Search
CPC ...... G16B 15/30; G06F 30/20; G06F 2111/10
See application file for complete search history.

(56) References Cited

U.S. PATENT DOCUMENTS

2002/0155501 A1 * 10/2002 Itai ........................... C07K 1/00
435/7.1

FOREIGN PATENT DOCUMENTS

| JP | 2005-18447 | 1/2005 |
|----|------------|--------|
| JP | 2006-209764 | 8/2006 |
| WO | 03/006154 | 1/2003 |

OTHER PUBLICATIONS

Tanida Y, Ito M, Fujitani H. Calculation of absolute free energy of binding for theophylline and its analogs to RNA aptamer using nonequilibrium work values. Chemical Physics. Aug. 16, 2007;337(1-3):135-43. (Year: 2007).*

Ward, Matthew S., Mohammad Ataai, Richard R. Koepsel, and Rex E. Shepherd. "Comparison of Energy-Minimized Structures of [Pdll (N-methyliminodiacetate)] Complexes of X1-His-X3-His-His Peptides as an Analysis of Steric and Specific Interactions with Synthetic Binding Tags for IMAC Separations." (Year: 2001).*

(Continued)

*Primary Examiner* — Chuen-Meei Gan
(74) *Attorney, Agent, or Firm* — Staas & Halsey LLP

(57) ABSTRACT

A method for searching for a modification site of a peptide molecule includes: calculating, by a computer, a second steric structure of the peptide molecule by using data of a first steric structure of the peptide molecule, the first steric structure being a steric structure of the peptide molecule in a complex structure of a target molecule and the peptide molecule, the second steric structure being a stable steric structure of the peptide molecule in a state where a steric configuration of a main chain of the peptide molecule in the first steric structure is fixe; and comparing data of the second steric structure with the data of the first steric structure in order to search for a side chain having a difference in steric configuration between the two steric structures.

9 Claims, 9 Drawing Sheets

(56) References Cited

OTHER PUBLICATIONS

Menchise, V., 2003. Insights into peptide nucleic acid (PNA) structural features: The crystal structure of a d-lysine-based chiral PNA-DNA duplex. Proceedings of the National Academy of Science. (Year: 2003).*

Ota N, Agard DA. Binding mode prediction for a flexible ligand in a flexible pocket using multi-conformation simulated annealing pseudo crystallographic refinement. Journal of Molecular Biology. Nov. 30, 2001;314(3):607-17. (Year: 2001).*

Extended European Search Report dated Feb. 16, 2021 from European Application No. 20193016.1, 16 pages.

Schueler-Furman et al., "Knowledge-based structure prediction of MHC class I bound peptides: a study of 23 complexes", Folding & Design/Structure, Cell Press, vol. 3, No. 6, Jan. 1, 1998, pp. 549-564.

Casiraghi et al., "Grafting Aminocyclopentane Carboxylic Acids onto the RGD Tripeptide Sequence Generates Low Nanomolar αvβ3/αvβ5 Integrin Dual Binders", Journal of Medicinal Chemistry, American Chemical Society, vol. 48, No. 24, Apr. 11, 2005 pp. 7675-7687.

Te et al., "Predicting the effects of amino acid replacements in peptide hormones on their binding affinities for class B GPCRs and application to the design of secretin receptor antagonists", Journal of Computer-Aided Molecular Design, Kluwer Academic Publishers, DO, vol. 26, No. 7, May 11, 2012, pp. 835-845.

Els et al., "An Aromatic Region To Induce a Switch between Agonism and Inverse Agonism at the Ghrelin Receptor", Journal of Medicinal Chemistry, vol. 55, No. 17, Sep. 13, 2012, pp. 7437-7449.

Pokharel et al., "Integrin activation by the lipid molecule 25-hydroxycholesterol induces a proinflammatory response", Nature Communications, vol. 10, No. 1, Apr. 1, 2019, 17 pages.

Mulligan et al., "Designing Peptides on a Quantum Computer", bioRxiv, Mar. 11, 2020, pp. 1-20.

Reina et al., "Computer-aided design of a PDZ domain to recognize new target sequences", Nature Structural Biology, vol. 9, No. 8, Jun. 24, 2002, 7 pages.

Ota et al., "Binding Mode Prediction for a Flexible Ligand in a Flexible Pocket using Multi-Conformation Simulated Annealing Pseudo Crystallographic Refinement", Journal of Molecular Biology, vol. 314, No. 3, Nov. 30, 2001, pp. 607-617.

Hao et al., "Torsion Angle Preference and Energetics of Small-Molecule Ligands Bound to Proteins", J. Chem. Inf. Model. 2007, 47, 2242-2252.

* cited by examiner

METHOD FOR SEARCHING FOR MODIFICATION SITE OF PEPTIDE MOLECULE AND INFORMATION PROCESSING APPARATUS

CROSS-REFERENCE TO RELATED APPLICATION

This application is based upon and claims the benefit of priority of the prior Japanese Patent Application No. 2019-191785, filed on Oct. 21, 2019, the entire contents of which are incorporated herein by reference.

FIELD

The embodiment discussed herein is related to a method and an apparatus for searching a modification site of a peptide molecule.

BACKGROUND

A binding free energy of a target molecule (for example, a protein) and a drug candidate molecule to a stable binding structure (also referred to as a complex structure) in a solvent is predicted by using a computer experiment. In a case where a drug candidate molecule is a low molecular compound, various methods for predicting the binding free energy have been studied.

Related techniques are disclosed in, for example, Japanese Laid-open Patent Publication No. 2006-209764 and Ming-Hong Hao, Omar Haq, and Ingo Muegge, "Torsion Angle Preference and Energetics of Small-Molecule Ligands Bound to Proteins", J. Chem. Inf. Model. 2007, 47, 2242-2252.

SUMMARY

According to an aspect of the embodiment, a method for searching for a modification site of a peptide molecule includes: calculating, by a computer, a second steric structure of the peptide molecule by using data of a first steric structure of the peptide molecule, the first steric structure being a steric structure of the peptide molecule in a complex structure of a target molecule and the peptide molecule, the second steric structure being a stable steric structure of the peptide molecule in a state where a steric configuration of a main chain of the peptide molecule in the first steric structure is fixe; and comparing data of the second steric structure with the data of the first steric structure in order to search for a side chain having a difference in steric configuration between the two steric structures.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENT

Figure 1:
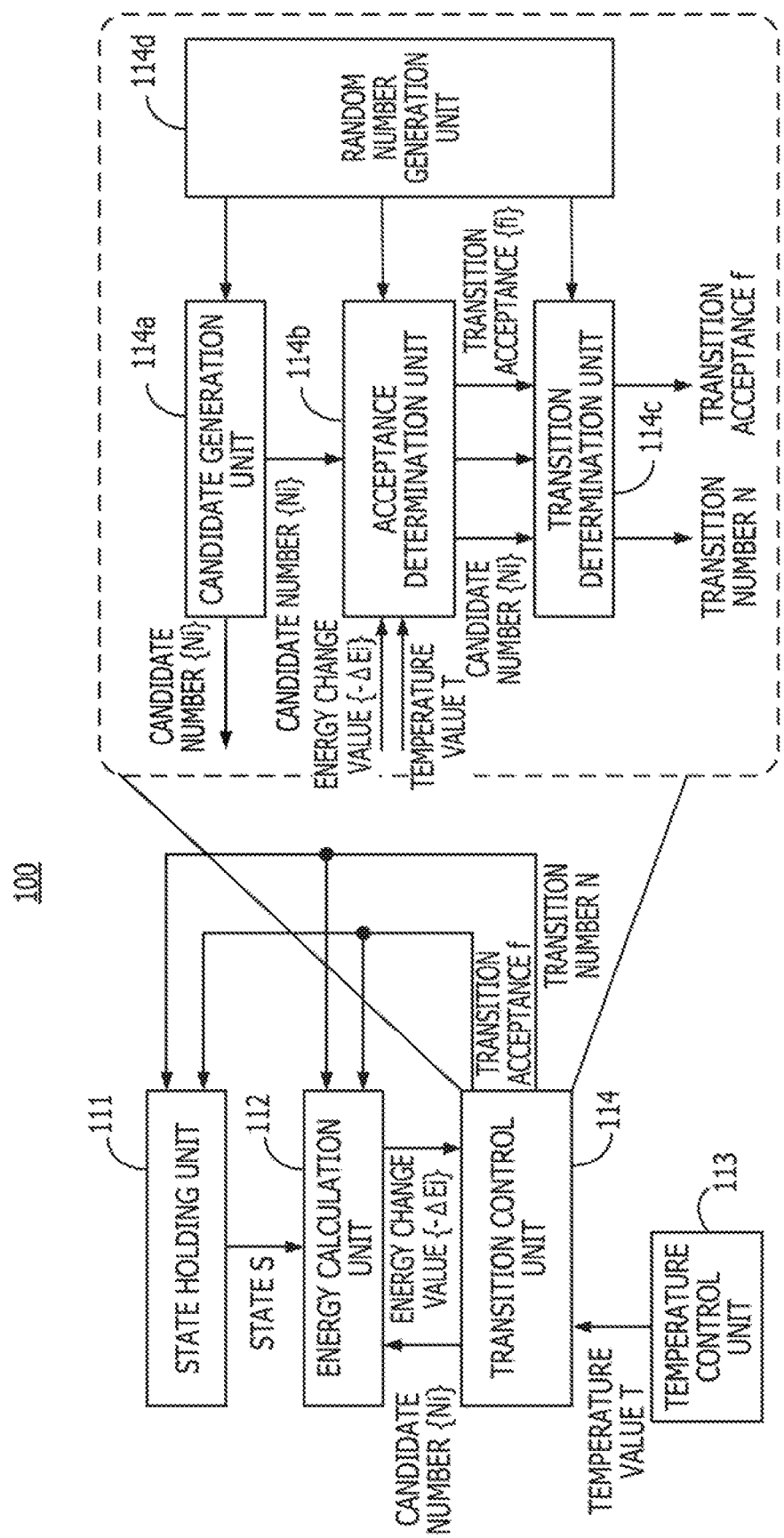
FIG. 1 is a diagram illustrating a configuration of an optimization apparatus (calculation unit) used in an annealing method.

However, in a case where the drug candidate molecule is a peptide molecule, sufficient sampling is difficult because both the target molecule and the drug candidate molecule have large structural fluctuations. Therefore, there has been no suitable methodology for predicting the binding free energy of a target molecule (for example, a protein) and a drug candidate molecule, which is a peptide molecule, to a binding structure in a solvent.

Nevertheless, development of new drugs using peptide molecules that have very large binding activity due to the flexibility of the structure as drug candidates has been actively conducted. In an actual development process, in a case where a peptide molecule having a certain degree of binding activity is found by an actual experiment, the peptide molecule is modified to enhance the binding activity. However, these operations are often carried out by the experience and intuition of researchers, and development may be delayed.

(Method for Searching for Modification Site of Peptide Molecule)

The disclosed method is a method of searching for a modification site of a peptide molecule using a computer (information processing apparatus).

The disclosed method includes a calculation process and a comparison process, and further includes other processes when appropriate.

In the calculation process, a stable steric structure of the peptide molecule, in a state where a steric configuration of a main chain of the peptide molecule in the steric structure is fixed, is calculated by using data of the steric structure of the peptide molecule in a complex structure of a target molecule and the peptide molecule.

In the comparison process, the calculated data of the stable steric structure of the peptide molecule is compared with the data of the steric structure of the peptide molecule in the complex structure to search for a side chain having a difference in steric configuration between two peptide molecules.

In a case where a modification site of a peptide molecule is intended to be searched for by existing simulation using a computer, electronic state calculation is performed on a system composed of the peptide molecule, a target molecule, and water molecules present around them, and a site to be modified in the peptide molecule is searched for. However, when this method is applied to a general system of equal to or more than one hundred thousand atoms, a calculation time of several years is used, which is not realistic.

In the development of new drugs using peptide molecules, it is important to know what the structure a drug candidate molecule has in a complex structure as quickly as possible. In a system having high binding activity, a molecule often takes a natural structure (stable steric structure) in a complex structure composed of the molecule and a target molecule.

Therefore, when the structure of the peptide molecule is a natural structure in the complex structure, the binding activity is considered to be large.

Amino acid residues configuring the peptide molecule are composed of a structure called a main chain and a structure called a side chain as described below.

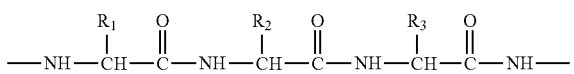

In the above-described formula, $R_1$, $R_2$, $R_3$ that are bonded to an alpha-carbon represent side chains. A portion other than the side chains is the main chain.

In a case where the peptide molecule and the target molecule form a complex structure, they are relatively stabilized by having a structure in which they may obtain benefits each other energetically. For peptide molecules, the steric configuration of the main chain distorted from its natural form due to formation of a complex structure is expected to affect the steric configuration of the side chains. Therefore, in a case where the stable steric configuration of the side chain under the distorted steric configuration of the main chain is different from the steric configuration of the side chain in the complex structure, it is considered that the side chain largely contributes to the structural stabilization of the complex structure. Such side chains are hereinafter referred to as hotspots.

It is considered that a structure of the hotspot is modified so that the structure of the peptide molecule in the complex structure approaches a more natural structure (stable steric structure), whereby the complex structure of the modified peptide molecule and the target molecule is more stabilized.

Therefore, in the disclosed technique, the following is performed.

The stable steric structure of the peptide molecule in the state of fixing the steric configuration of the main chain of the peptide molecule in the steric structure is calculated by using the steric structure data of the peptide molecule in the complex structure of the target molecule and the peptide molecule.

The calculated data of the stable steric structure of the peptide molecule is compared with the data of the steric structure of the peptide molecule in the complex structure to search for a side chain having a difference in steric configuration between two peptide molecules.

In the disclosed technique, the electronic state calculation may not be performed when searching for a site where the contribution of binding is large. Therefore, in the disclosed technique, it is possible to efficiently search for a modification site of a peptide molecule.

<Calculation Process>

In the calculation process, the stable steric structure of the peptide molecule, in a state where the steric configuration of the main chain of the peptide molecule in the steric structure is fixed, is calculated by using the data of the steric structure of the peptide molecule in the complex structure of the target molecule and the peptide molecule.

<<Target Molecule>>

The target molecule is not particularly limited and may be appropriately selected depending on the intended purpose, and examples thereof include proteins, ribonucleic acids (RNA), deoxyribonucleic acids (DNA), and the like.

<<Peptide Molecule>>

A peptide molecule is a molecule in which amino acids as monomers are linked in a short chain by a peptide bond.

Peptide molecules may be cyclic molecules or non-cyclic molecules.

The number of amino acids constituting the peptide molecule is not particularly limited and may be appropriately selected depending on the intended purpose, for example, the number may be equal to or more than 5 and equal to or less than 100, equal to or more than 5 and equal to or less than 50, equal to or more than 10 and equal to or less than 50, or equal to or more than 10 and equal to or less than 30.

The amino acid may be a naturally occurring amino acid or a non-naturally occurring amino acid as long as it is an organic compound having a functional group of both an amino group and a carboxyl group.

Examples of amino acid include:
Glycine (Gly)
Proline (Pro)
Alanine (Ala)
Arginine (Arg)
Asparagine (Asn)
Aspartic acid (Asp)
Cysteine (Cys)
Glutamine (Gin)
Glutamic acid (Glu)
Histidine (His)
Isoleucine (Ile)
Leucine (Leu)
Lysine (Lys)
Methionine (Met)
Phenylalanine (Phe)
Serine (Ser)
Threonine (Thr)
Tryptophan (Trp)
Tyrosine (Tyr)
Valine (Val)
Ornithine (Orn)
Selenocysteine (Sec)
Pyrrolidine (Pyl)
Norvaline
Norleucine
Citrulline
Creatine
Cystine
Thyroxine
Phosphoserine A molecular weight of the amino acid is not particularly limited and may be appropriately selected depending on the intended purpose, provided that it is, for example, equal to or more than 89, which is a molecular weight of alanine, and, for example, the molecular weight of the amino acid may be equal to or more than 89 and equal to or less than 500, or equal to or more than 89 and equal to or less than 300.

<<Complex Structure>>

The complex structure of the target molecule and the peptide molecule is a stable structure.

The complex structure may be a known complex structure in which the stable structure is a known or an unknown complex structure in which the stable structure is not known.

Examples of the known complex structures include complex structures recorded in known databases. In the known databases, for example, experimental data of a complex structure of a target molecule (receptor) and a molecule (ligand) obtained from experiments such as X-ray crystallography, nuclear magnetic resonance (NMR) analysis, and analysis using a Cryo-electron microscope is recorded.

Examples of the known databases include Protein Data Bank (PDB) and the like.

The unknown complex structure may be obtained using, for example, a molecular mechanics method, a molecular dynamics method, or the like. Among them, the molecular dynamics method is preferable.

The molecular dynamics (MD) method means a method of simulating the motion of particles (mass points) such as atoms by numerically solving Newton's equation of motion.

The molecular dynamics calculation (simulation) by the molecular dynamics method may be performed using, for example, a molecular dynamics calculating program. Examples of the molecular dynamics calculating program include AMBER, CHARMm, GROMACS, GROMOS, NAMD, myPresto, and the like.

In the molecular dynamics calculation, a binding structure may be relaxed to a thermal equilibrium state or a state close to the thermal equilibrium state, for example, by performing calculation under a certain temperature and pressure condition (NPT ensemble).

The steric structure data includes, for example, atomic information data, coordinate information data, and binding information data, and constructs a steric structure in a coordinate space.

A data format is not particularly limited and may be appropriately selected depending on the intended purpose, and for example, the data format may be text data, a structure data file (SDF) format, or an MOL file format.

The atomic information data is data on the type of atom.

The coordinate information data is data on coordinates (positions) of atoms.

The binding information data is data on a bond between atoms.

In the calculation process, the stable steric structure of the peptide molecule, in a state where the steric configuration of the main chain of the peptide molecule in the steric structure of the peptide molecule in the complex structure is fixed, is calculated.

In the calculation of the stable steric structure of the peptide molecule, for example, a relative permittivity around the peptide molecule is set in consideration of a relative permittivity around the peptide molecule in the complex structure. The consideration here means, for example, matching or approximating the relative permittivity around the peptide molecule to the relative permittivity around the peptide molecule in the complex structure. The relative permittivity around the peptide molecule is set to, for example, four.

The method for calculating the stable steric structure of the peptide molecule, in a state in which the steric configuration of the main chain is fixed, is not particularly limited and may be appropriately selected depending on the intended purpose, however, it is preferable to calculate a minimum energy of an Ising model by performing a ground state search using an annealing method on the Ising model converted based on restriction conditions of the side chain of the peptide molecule.

By fixing the steric configuration of the main chain, the search for a stable steric structure of the peptide molecule may be reduced to a combinatorial optimization problem of the steric configuration of the side chain. Therefore, the minimum energy of the Ising model may be calculated. The calculation of the minimum energy of the Ising model is a method that may be performed in a very short time among methods of exhaustively searching for a stable steric structure of a peptide molecule in a state where the steric configuration of the main chain is fixed. Therefore, this greatly contributes to more efficiently performing the disclosed technique.

The energy equation of the Ising model may be expressed, for example, by the following equation.

$$\mathcal{H} = A \cdot \left[ -\sum_i \left( \sum_j W_{ij} + b_i \right) \right] \cdot x_i + B \cdot \sum_{res} \sum_{rot} (x_k - 1)^2$$

In the equation, $W_{ij}$ represents a side chain-side chain interaction, $b_i$ represents a main chain-side chain interaction at the amino acid residue. $x_i$ represents bits of a rotor state of the side chain. "res" represents an amino acid residue. "rot" represents the rotation of the side chain. $x_k$ represents bits of the rotor state of the k-th amino acid residue. A represents a positive number. B represents a positive number.

The minimum energy of the Ising model may be calculated using an annealing machine. The annealing machine is not particularly limited and may be appropriately selected depending on the intended purpose as long as it is a computer that employs an annealing method of performing a ground state search for an energy function represented by an Ising model, and the annealing machine may be a quantum annealing machine, a semiconductor annealing machine using semiconductor technology, or simulated annealing executed by software using a central processing unit (CPU) or a graphics processing unit (GPU).

An example of an annealing method and an annealing machine will be described below.

The annealing method (simulated annealing method, SA method) is a kind of Monte Carlo method, and is a method of probabilistically obtaining a solution by using a random number value. Hereinafter, an object of minimizing a value of an evaluation function to be optimized will be described as an example, and the value of the evaluation function will be referred to as energy. In a case of maximization, a sign of the evaluation function may be changed.

First, starting with an initial state in which one discrete value is assigned to an individual variable, a state transition from the current state (a combination of values of variables) to a state close to the current state (for example, a state in which only one of the variables has been changed) is examined. A change in energy associated with the state transition is calculated, and it is stochastically determined whether to adopt the state transition and change the current state or to maintain the current state without adopting the state transition, according to the calculated value. When setting an adoption probability of a state transition that results in a drop in the energy to be greater than that of a state transition that results in a rise in the energy, a state change occurs in a direction in which the energy drops on average, and thus it is possible to expect that the state is transitioned to a more suitable state with the lapse of time. Finally, an optimal solution or an approximate solution that possibly results in energy close to that of the optimal solution may be obtained. When a state transition that results in a drop in the energy in a deterministic way is adopted and a state transition that results in a rise in the energy is not adopted, the change in energy broadly and monotonically decreases over time, however, once a local solution is reached, no further change may occur. Since an extraordinarily large number of local solutions are present in a discrete optimization problem as described above, in many cases the state gets stuck at a local solution that is not very close to an optimal solution. Therefore, it is important to stochastically decide whether it is adopted.

In the annealing method, it has been proven that the state reaches the optimal solution at a limit of infinite time (the number of iterations) when the adoption (acceptance) probability of the state transition is determined as follows.

(1) For an energy change (energy decrease) value $(-\Delta E)$ associated with a state transition, an acceptance probability p of the state transition is determined by any of the following functions f( ).

$$p(\Delta E, T) = f(-\Delta E / T) \quad \text{(Formula 1-1)}$$

$$f_{metro}(x) = \min(1, e^x) \text{ (Metropolis method)} \quad \text{(Formula 1-2)}$$

$$f_{Gibbs}(x) = \frac{1}{1 + e^{-x}} \text{ (Gibbs method)} \quad \text{(Formula 1-3)}$$

T is a parameter called a temperature value and is changed as follows.

(2) The temperature value T is logarithmically reduced with respect to the number of iterations t as expressed by the following equation.

$$T = \frac{T_0 \log(c)}{\log(t + c)} \quad \text{(Formula 2)}$$

$T_0$ represents an initial temperature value and it is desirable that a sufficiently large value be set in accordance with the problem.

In a case of using the acceptance probability expressed by the Formulas in (1), when a steady state is reached after sufficient number of iterations, an occupation probability of an individual state is in accordance with a Boltzmann distribution with respect to a thermal equilibrium state in thermodynamics. Since the occupation probability of a lower-energy state increases when the temperature is gradually lowered from a high initial temperature, a low-energy state is supposed to be obtained when the temperature has sufficiently decreased. This method is referred to as an annealing method (or pseudo-annealing method) because this behavior resembles state change when annealing a material. The stochastic occurrence of a state transition that results in a rise in the energy corresponds to thermal excitation in physics.

FIG. 1 illustrates a conceptual configuration of an optimization apparatus (calculation unit) that performs the annealing method. Although cases where a plurality of candidates for the state transition is generated will be also described in the following description, the transition candidates are generated one by one in the normal basic annealing method.

An optimization apparatus 100 includes a state holding unit 111 configured to hold a current state S (values of a plurality of state variables). The optimization apparatus 100 also includes an energy calculation unit 112 configured to calculate energy change values $\{-\Delta Ei\}$ of state transitions in a case where the state transition occurs from the current state S as a result of change in any of the values of the plurality of state variables. The optimization apparatus 100 includes a temperature control unit 113 configured to control a temperature value T and a transition control unit 114 configured to control state changes.

The transition control unit 114 stochastically determines whether or not any one of a plurality of state transitions is accepted depending on a relative relationship between the energy change values $\{-\Delta Ei\}$ and thermal excitation energy, based on the temperature value T, the energy change values $\{-Mi\}$, and the random number value.

When the transition control unit 114 is subdivided, the transition control unit 114 includes a candidate generation unit 114a for generating a candidate for a state transition, and an acceptance determination unit 114b for stochastically determining for each candidate whether or not the state transition is accepted based on the energy change values $\{-\Delta Ei\}$ of the candidates and the temperature value T. The transition control unit 114 further includes a transition determination unit 114c for determining a candidate to be adopted from the accepted candidates, and a random number generation unit 114d for generating a probability variable.

The operation in one iteration is as follows. First, the candidate generation unit 114a generates one or a plurality of candidates (candidate numbers {Ni}) for the state transition from the current state S held by the state holding unit 111 to the next state. The energy calculation unit 112 calculates energy change values $\{-\Delta Ei\}$ for each of the state transitions for the candidates, by using the current state S and the candidates for the state transition. The acceptance determination unit 114b uses the temperature value T generated in the temperature control unit 113 and a probability variable (random number value) generated by the random number generation unit 114d, and accepts the state transition with the acceptance probability expressed by the above Formulas in (1) according to the energy change values $\{-\Delta Ei\}$ of the respective state transitions. The acceptance determination unit 114b outputs the acceptances {fi} of the respective state transitions. In a case where a plurality of state transitions is accepted, the transition determination unit 114c randomly selects one thereof by using a random number value. The transition determination unit 114c then outputs a transition number N of the selected state transition, and a transition acceptance f. In a case where there is an accepted state transition, the values of the state variable stored in the state holding unit 111 is updated according to the adopted state transition.

Starting with an initial state, the above-described iteration is repeated while causing the temperature control unit 113 to lower the temperature value, and the operation ends when an end determination condition, for example, a certain number of iterations is reached, or the energy becomes lower than a predetermined value, is satisfied. The solution outputted by the optimization apparatus 110 is the state corresponding to the end of the operation.

Figure 2:
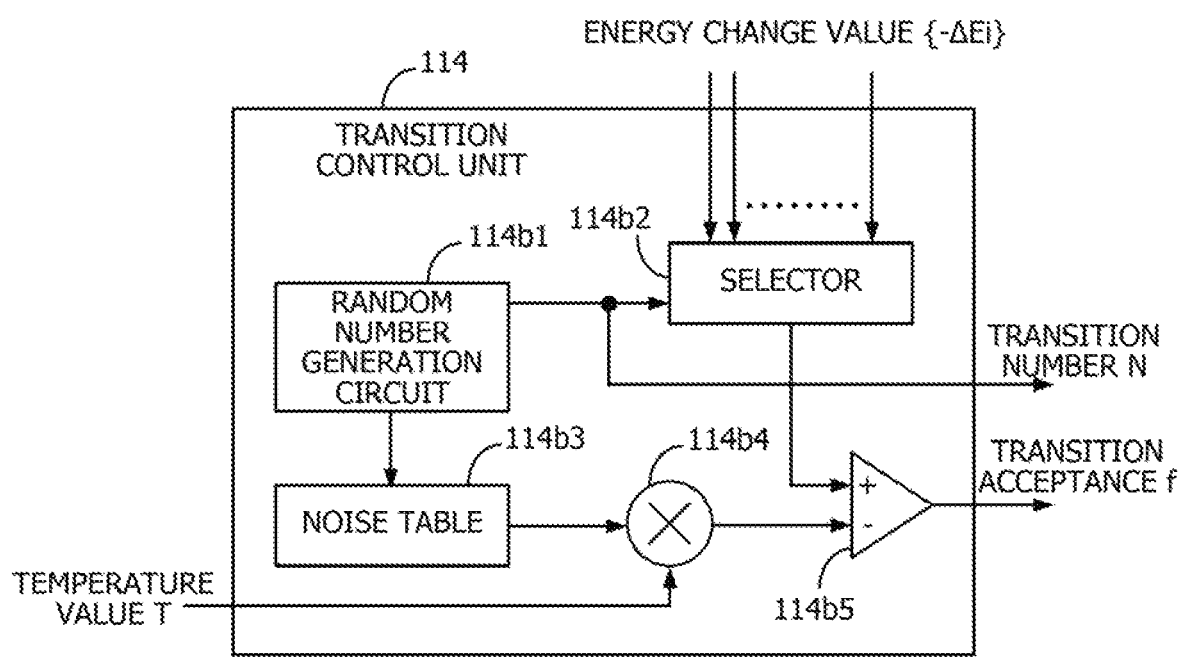
FIG. 2 is a circuit level block diagram of a transition control unit.

FIG. 2 is a circuit level block diagram of a configuration example of a transition control unit in a normal annealing method for generating candidates one by one, especially, an arithmetic portion used for an acceptance determination unit.

The transition control unit 114 includes a random number generation circuit 114b1, a selector 114b2, a noise table 114b3, a multiplier 114b4, and a comparator 114b5.

Of the energy change values $\{-\Delta Ei\}$ calculated for the candidates of the respective state transitions, the selector 114b2 selects and outputs an energy change value corresponding to the transition number N, which is a random number value generated by the random number generation circuit 114b1.

Functions of the noise table 114b3 will be described later. As the noise table 114b3, for example, a memory such as a random-access memory (RAM) or a flash memory may be used.

The multiplier 114b4 outputs a product obtained by multiplying a value outputted by the noise table 114b3 by the temperature value T (corresponding to the thermal excitation energy described above).

The comparator 114b5 outputs a comparison result in which a multiplication result outputted by the multiplier 114b4 is compared with an energy change value −ΔE selected by the selector 114b2, as the transition acceptance f.

The transition control unit 114 illustrated in FIG. 2 basically implements the above-described function as is, but the mechanism for permitting the state transition with the acceptance probability expressed by Formulas in (1) has not been described so far, and therefore, this will be supplemented.

A circuit that outputs 1 at the acceptance probability p and outputs 0 at the probability (1-p) may be realized by a comparator that has two inputs A and B, and outputs 1 when A>B, and outputs 0 when A<B by inputting the acceptance probability p to the input A and a uniform random number having a value in a section [0, 1) to the input B. Thus, with an input of the value of the acceptance probability p calculated by using Formulas in (1) based on the energy change value and the temperature value T to the input A of the comparator, it is possible to realize the above function.

Specifically, assuming that f is the function used in Formulas in (1), and that u is a uniform random number having a value in the section [0, 1), a circuit that outputs 1 when $f(\Delta E/T)$ is greater than u realizes the above function.

The situation may be accepted, however, the same function may be realized by the following modification. Even when the same monotonically increasing function is applied to two numbers, the two numbers maintain the same magnitude relationship. Therefore, even when the same monotonically increasing function is applied to the two inputs of the comparator, the same output is obtained. When an inverse function $f^{-1}$ off is adopted as this monotonically increasing function, it is seen that a circuit that outputs 1 when $-\Delta E/T$ is greater than $f^{-1}(u)$ may be adopted. Since the temperature value T is positive, it is seen that a circuit that outputs 1 when $-\Delta E$ is greater than $Tf^{-1}(u)$ may be adopted. The noise table 114b3 in FIG. 2 is a conversion table for realizing the inverse function $f^{-1}(u)$, and is a table for outputting a value of the following function with respect to the input obtained by discretizing the section [0, 1).

$$f_{metro}^{-1}(u) = \log(u) \quad \text{(Formula 3-1)}$$

$$f_{Gibbs}^{-1}(u) = \log\left(\frac{u}{1-u}\right) \quad \text{(Formula 3-2)}$$

Although the transition control unit 114 includes a latch that holds a determination result and the like, a state machine that generates the corresponding timing, and the like, these components are not illustrated in FIG. 2 for simple illustration.

Figure 3:
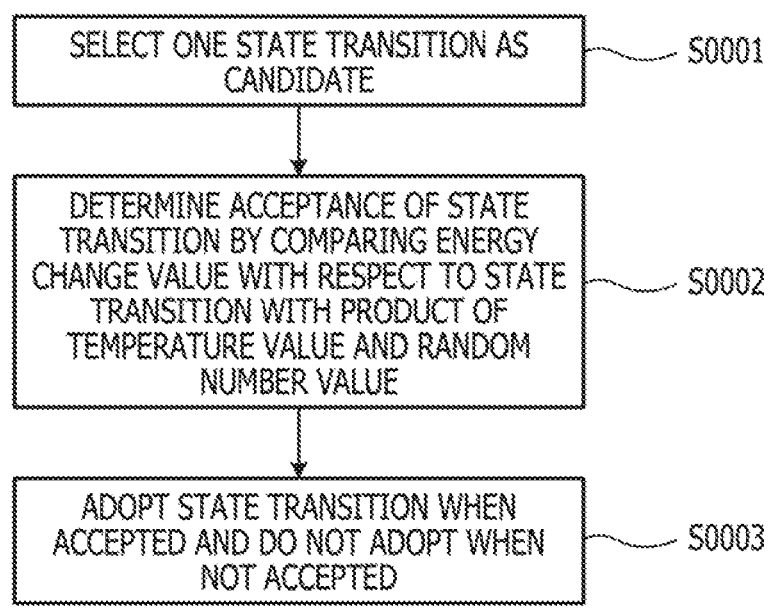
FIG. 3 is a diagram illustrating an operation flow of the transition control unit.

FIG. 3 illustrates the flow of operation of the transition control unit 114. The flow of operation includes a step of selecting one state transition as a candidate (S0001), a step of determining whether a state transition is accepted or not by comparing the energy change value with respect to the state transition with a product of a temperature value and a random number value (S0002), and a step in which the state transition is adopted when the state transition is accepted, and the state transition is not adopted when the state transition is not accepted (S0003).

<Comparison Process>

In the comparison process, the calculated data of the stable steric structure of the peptide molecule is compared with the data of the steric structure of the peptide molecule in the complex structure to search for a side chain having a difference in steric configuration between two peptide molecules.

The comparison is preferably performed by visualizing the stable steric structure of the peptide molecule and the steric structure of the peptide molecule in the complex structure. In doing so, the side chain having a difference in steric configuration between two peptide molecules may be easily found.

The method for visualizing the steric structure of the peptide molecule is not particularly limited and may be appropriately selected depending on the intended purpose, and may be performed using known molecular graphic software. Examples of the molecular graphic software include, for example, PyMOL, and the like.

Visualization may be performed, for example, by incorporating the steric structure data of the peptide molecule into molecular graphic software to construct a steric structure, and displaying the created steric structure on a display device.

The comparison is preferably performed by superposing the main chain of the visualized stable steric structure of the peptide molecule with the main chain of the visualized steric structure of the peptide molecule. In this way, the side chain having a difference in steric configuration between the two peptide molecules may be found more easily.

The superposition of the main chains may be carried out, for example, by overlapping a Cα atom of each amino acid residue in the peptide molecule and overlapping a Cβ atom of the side chain.

The superposition of the main chains may be carried out using, for example, molecular graphic software. Examples of the molecular graphic software include, for example, PyMOL, and the like.

In the comparison process, for example, a side chain (hotspot) that largely contributes to the structural stabilization of the complex structure is specified from the side chain having a difference in steric configuration between two peptide molecules.

The identification of the hotspot may be appropriately determined from the side chain having a difference in steric configuration between two peptide molecules. For example, when the calculated stable steric structure of the peptide molecule is superimposed on the steric structure of the peptide molecule of the complex structure so that the main chains of the two peptide molecules overlap, in a case where the side chain of the calculated peptide molecule overlaps a binding site of the target molecule of the complex structure (the site where the peptide molecule binds to the target molecule), the side chain is specified as a hotspot.

The side chain in the peptide molecule of the complex structure corresponding to the side chain overlapping the binding site is likely to interfere with the structural stabilization of the complex structure. Specifically, the side chain is likely to be a hotspot.

The disclosed technique will be described using a flowchart.

Figure 4:
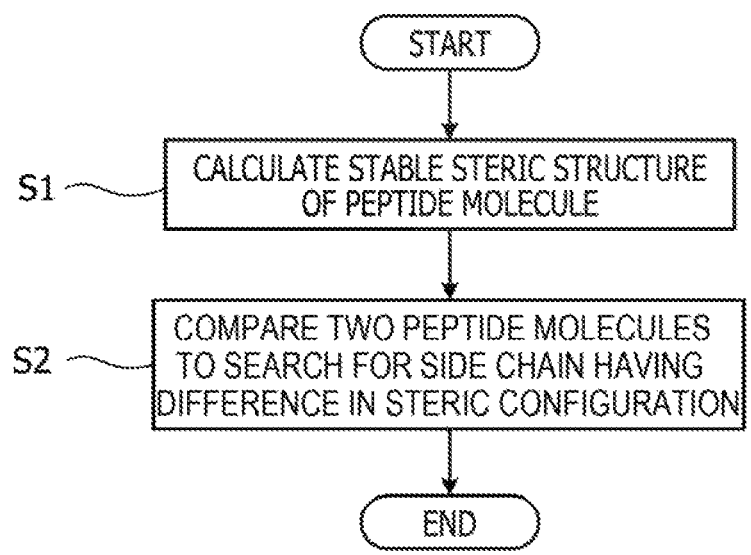
FIG. 4 is a flowchart of an example of a disclosed technique.

FIG. 4 is an example of a flow chart of the disclosed technique.

<Step S1>

First, the stable steric structure of the peptide molecule, in a state where the steric configuration of the main chain of the peptide molecule in the steric structure is fixed, is calculated using data of the steric structure of the peptide molecule in the complex structure of the target molecule and the peptide molecule (S1).

The data of the steric structure of the peptide molecule in the complex structure may be acquired from data of the complex structure recorded in a known database. Examples of the known databases include Protein Data Bank (PDB) and the like.

The calculation of the stable steric structure is preferably performed, for example, by performing a ground state search using an annealing method on the Ising model converted based on the restriction conditions of the side chain of the peptide molecule to calculate the minimum energy of the Ising model.

<Step S2>

Next, the calculated data of the stable steric structure of the peptide molecule is compared with the data of the steric structure of the peptide molecule in the complex structure to search for a side chain having a difference in steric configuration between the two peptide molecules (S2).

The comparison is performed by visualizing the stable steric structure of the peptide molecule and the steric structure of the peptide molecule in the complex structure using, for example, molecular graphic software.

Thus, the side chain of the peptide molecule to be modified for stabilizing the complex structure may be efficiently found.

An example of experimental results of the method of the disclosed technology is described below.

Figure 5A:
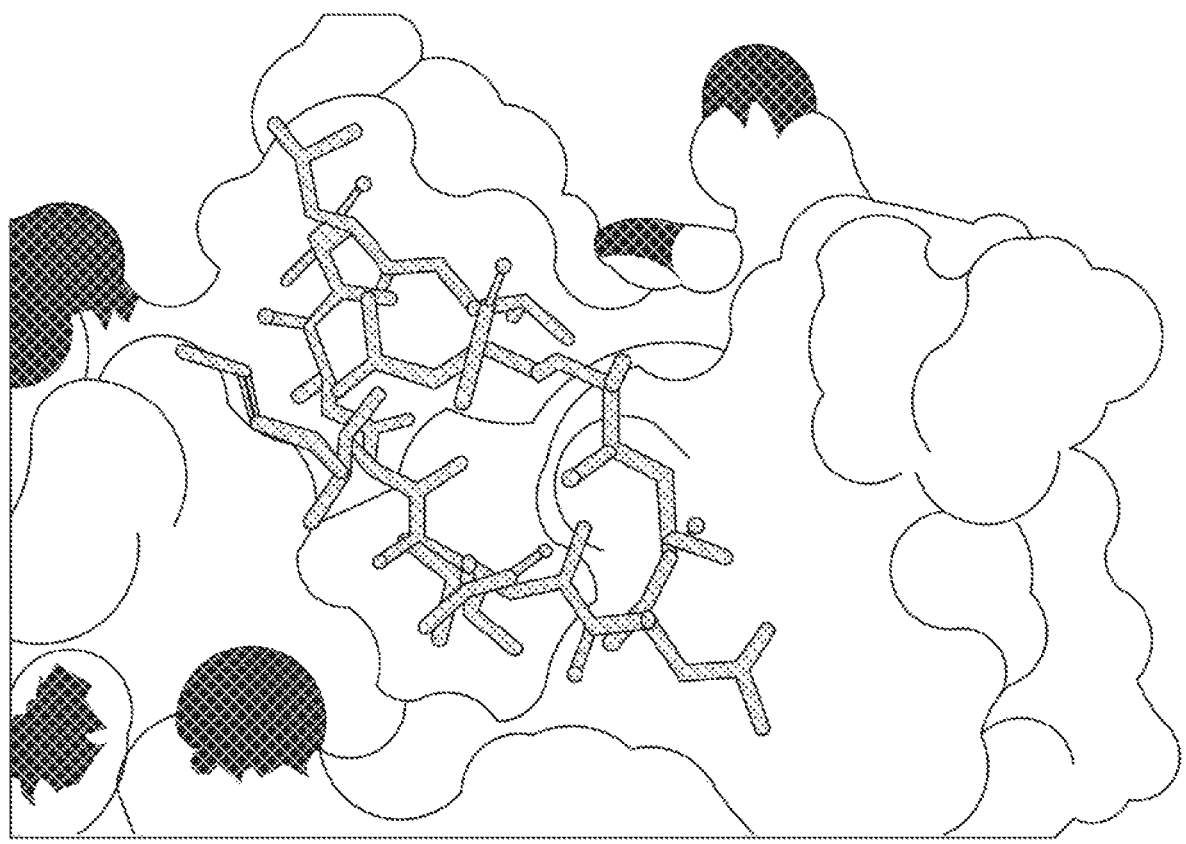
FIG. 5A is a schematic view of an example of a complex structure (1WCA)

FIG. 5A is the complex structure of 1WCA in PDB. The protein is CYCLOPHILIN A (CypA) and the peptide molecule is CYCLOSPORIN A (CsA).

Using the peptide molecule having the complex structure illustrated in FIG. 5A, the stable steric structure of the peptide molecule was calculated in a state where the steric configuration of the main chain of the peptide molecule was fixed.

The calculated stable steric structure of the peptide molecule and the steric structure of the peptide molecule in the complex structure were visualized in a state where the main chains were overlapped. The results are illustrated in FIG. 5B.

Figure 5B:
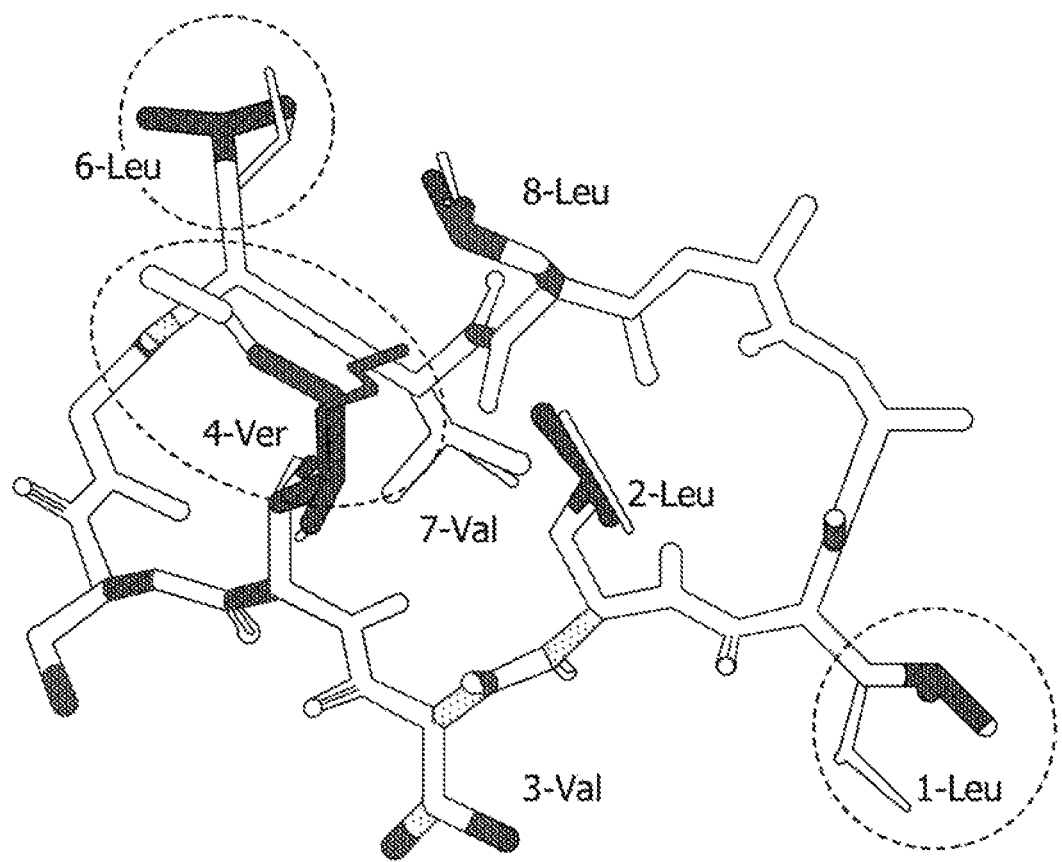
FIG. 5B is a diagram in which two peptide molecules are overlapped.

In FIG. 5B, the main chains of the two peptide molecules to be compared overlap, and some side chains have a difference in steric configuration. The side chains of 1-Leu, 4-Ver, and 6-Leu that are indicated by circles have a large difference in steric configuration and are likely to be hotspots. The calculated structure of the side chain of the peptide molecule is indicated by a relatively thin line.

(Program)

The disclosed program is a program for causing a computer to execute the disclosed method for searching for a modification site of a peptide molecule, The program may be created using various known program languages according to a configuration of a computer system to be used, and a type, a version, and the like of an operating system.

The program may be recorded using a recording medium such as an internal hard disk or an external hard disk, or may be recorded using a recording medium such as a compact disc read-only memory (CD-ROM), a digital versatile disk read-only memory (DVD-ROM), a magneto-optical disk (MO disk), or a Universal Serial Bus (USB) memory [USB flash drive]. When the program is recorded using a recording medium such as a CD-ROM, a DVD-ROM, an MO disk, or a USB memory, the program may be used directly or by being installed on a hard disk through a recording medium reading device included in the computer system when appropriate. The program may be also recorded in an external storage area (another computer or the like) accessible from the computer system through the information communication network, and the program may be used directly from the external storage area through the information communication network or by being installed on the hard disk when appropriate.

The program may be recorded using a plurality of recording media while being divided for each arbitrary process.

(Recording Medium)

The disclosed recording medium records the disclosed program.

The disclosed recording medium is computer-readable.

The disclosed recording medium may be transitory or non-transitory.

The disclosed recording medium is, for example, a recording medium having recorded thereon a program for causing a computer to execute the disclosed method for searching for a modification site of a peptide molecule.

The recording medium is not particularly limited, and may be appropriately selected according to the purpose, and examples thereof include, for example, an internal hard disk, an external hard disk, a CD-ROM, a DVD-ROM, an MO disk, a USB memory, and the like.

The recording medium may be a plurality of recording media in which the program is divided and recorded for each arbitrary process.

(Apparatus for Searching for Modification Site of Peptide Molecule)

The disclosed apparatus for searching for a modification site of a peptide molecule includes at least a calculation unit and a comparison unit, and further includes other units when appropriate.

The calculation unit, by using data of the steric structure of the peptide molecule in the complex structure of the target molecule and the peptide molecule, calculates the stable steric structure of the peptide molecule in a state in which the steric configuration of the main chain of the peptide molecule in the steric structure is fixed.

The comparison unit compares the calculated data of the stable steric structure of the peptide molecule with the data of the steric structure of the peptide molecule in the complex structure to search for a side chain having a difference in steric configuration between two peptide molecules.

An aspect of the calculation unit is the same as the aspect of the calculation process in the disclosed method for searching for a modification site of a peptide molecule.

An aspect of the comparison unit is the same as the aspect of the comparison process in the disclosed method for searching for a modification site of a peptide molecule.

The disclosed apparatus for searching for a modification site of a peptide molecule includes, for example, a memory, a processor, and other units when appropriate.

The memory stores, for example, data of a complex structure of a target molecule and a peptide molecule.

The memory stores, for example, data of the steric structure of the peptide molecule in the complex structure.

The memory stores, for example, data of the calculated stable steric structure of the peptide molecule.

The processor is coupled to the memory.

The processor is configured to use the data of the steric structure of the peptide molecule in the complex structure of the target molecule and the peptide molecule to calculate a stable steric structure of the peptide molecule in a state where the steric configuration of the main chain of the peptide molecule in the steric structure is fixed.

The processor is configured to compare the calculated data of the stable steric structure of the peptide molecule with the data of the steric structure of the peptide molecule in the complex structure to search for a side chain having a difference in steric configuration between two peptide molecules.

The processor is, for example, a CPU, a GPU, or a combination thereof.

Figure 6:
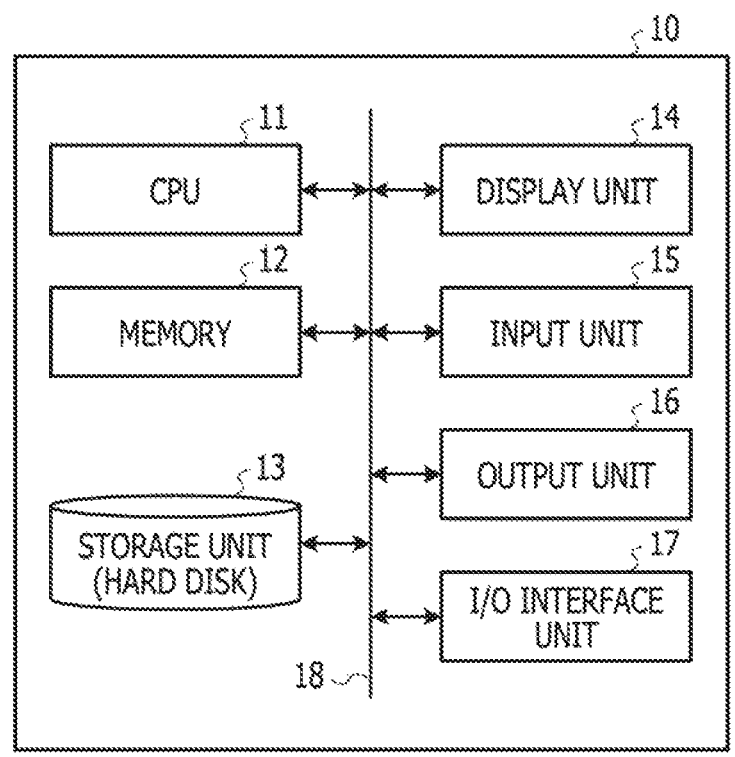
FIG. 6 is a configuration example of a disclosed apparatus for searching for a modification site of a peptide molecule.

FIG. 6 illustrates a configuration example of a disclosed apparatus for searching for a modification site of a peptide molecule.

The apparatus 10 is configured, for example, by a CPU 11, a memory 12, a storage unit 13, a display unit 14, an input unit 15, an output unit 16, an I/O interface unit 17, and the like that are coupled via a system bus 18.

The CPU 11 performs operations (four arithmetic operations, comparison operations, and the like), operation control of hardware and software, and the like.

The memory 12 is a memory such as a RAM, a read-only memory (ROM), or the like. The RAM stores an operating system (OS), an application program, and the like read from the ROM and the storage unit 13, and functions as a main memory and a work area of the CPU 11.

The storage unit 13 is a device for storing various programs and data, and is a hard disk, for example. The storage unit 13 stores a program to be executed by the CPU 11, data to be used for execution of the program, the OS, and the like.

The program is stored in the storage unit 13, loaded into the RAM (main memory) of the memory 12, and executed by the CPU 11.

The display unit 14 is a display device, and is, for example, a display device such as a CRT monitor, a liquid crystal panel, or the like.

The input unit 15 is an input device for various data, and is, for example, a keyboard, a pointing device (for example, a mouse, or the like), or the like.

The output unit 16 is an output device for various data, and is, for example, a printer, or the like.

The I/O interface unit 17 is an interface for coupling various external devices. For example, the I/O interface unit 17 enables input and output of data of a CD-ROM, a DVD-ROM, an MO disk, a USB memory, or the like.

Figure 7:
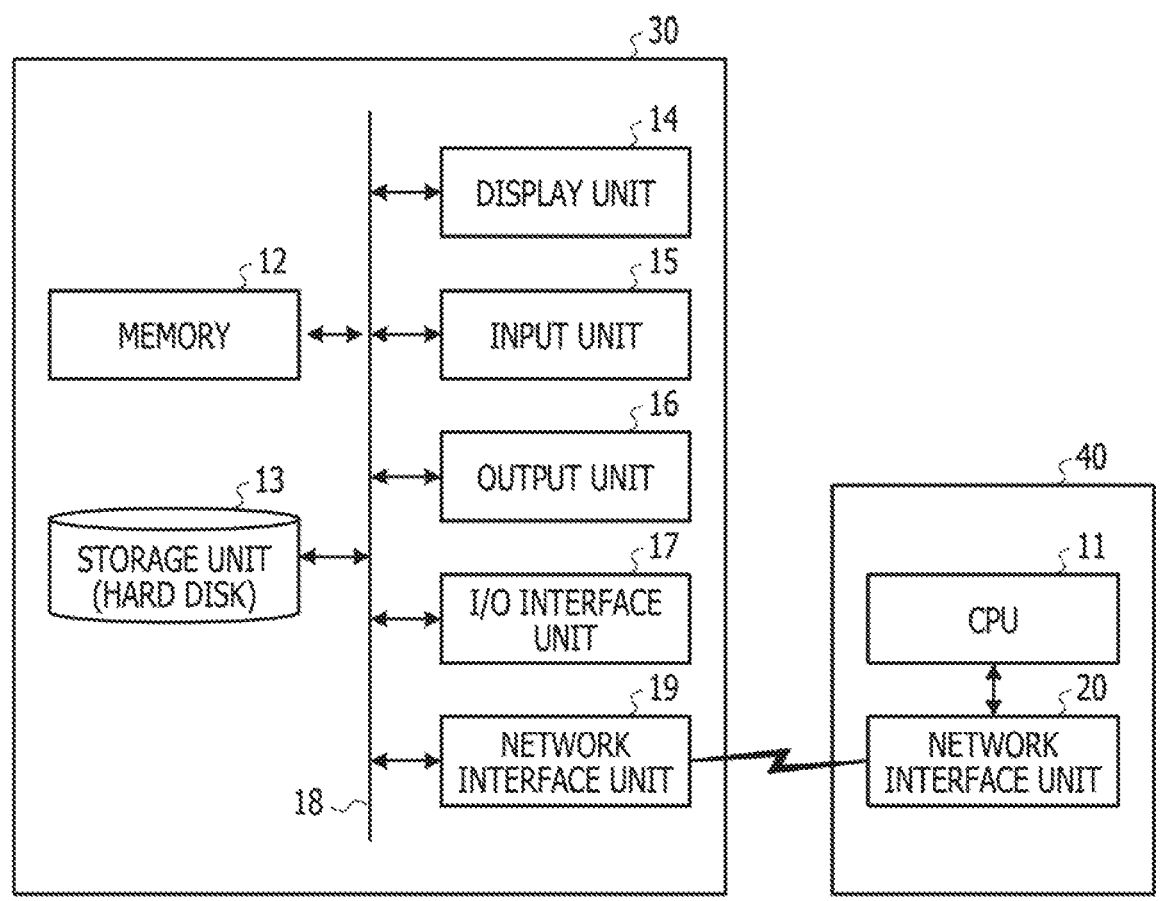
FIG. 7 is another configuration example of the disclosed apparatus for searching for the modification site of the peptide molecule.

FIG. 7 illustrates another example of the configuration of the disclosed apparatus for searching for a modification site of a peptide molecule.

The configuration example of FIG. 7 is a cloud-type configuration example, and the CPU 11 is independent of the storage unit 13 and the like. In the configuration example, a computer 30 that stores the storage unit 13 and the like, and a computer 40 that stores the CPU 11 are coupled via network interface units 19 and 20.

The network interface units 19 and 20 are hardware configured to perform communication by using the Internet.

Figure 8:
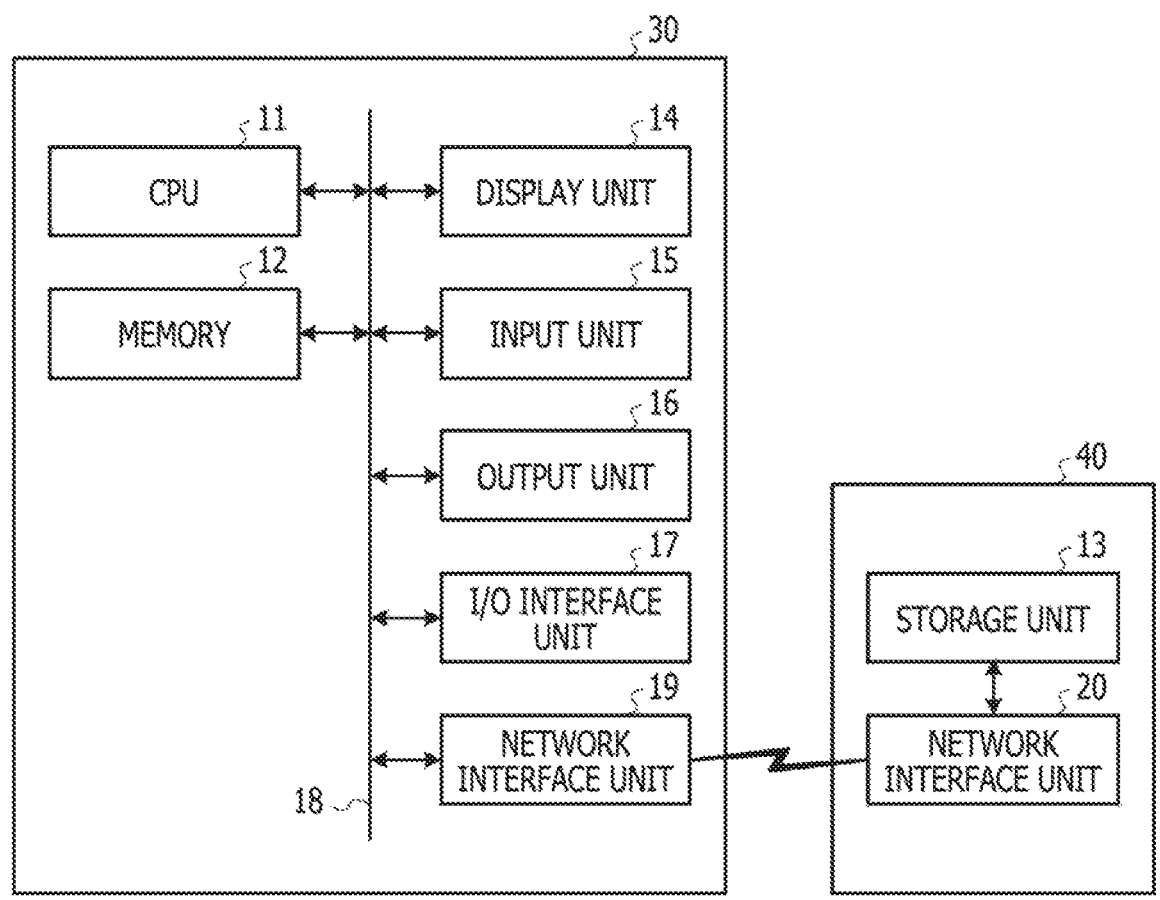
FIG. 8 is another configuration example of the disclosed apparatus for searching for the modification site of the peptide molecule.

FIG. 8 illustrates another example of the configuration of the disclosed apparatus for searching for a modification site of a peptide molecule.

The configuration example of FIG. 8 is a cloud-type configuration example, and the storage unit 13 is independent of the CPU 11 and the like. In the configuration example, the computer 30 that stores the CPU 11 and the like, and the computer 40 that stores the storage unit 13 are coupled via the network interface units 19 and 20.

According to the disclosed method for searching for a modification site of a peptide molecule, the above-described problems in the related art may be solved, and a modification site of a peptide molecule may be efficiently searched for.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A method for searching for a modification site of a peptide molecule, the method comprising:
    calculating, by a computer, a second steric structure of the peptide molecule by using data of a first steric structure of the peptide molecule, the first steric structure being a steric structure of the peptide molecule in a complex structure of a target molecule and the peptide molecule, the second steric structure being a stable steric structure of the peptide molecule in a state where a steric configuration of a main chain of the peptide molecule in the first steric structure is fixed, wherein the calculating the second steric structure further includes performing a ground state search using an annealing method for an Ising model converted based on a restriction condition of a side chain of the peptide molecule to calculate a minimum energy of the Ising model and to reduce computational cost; and
    comparing data of the second steric structure with the data of the first steric structure in order to search for a side chain having a difference in steric configuration between the two steric structures.

2. The method according to claim 1, further comprising:
    visualizing the second steric structure and the first steric structure to compare the data of the second steric structure with the data of the first steric structure.

3. The method according to claim 2, further comprising:
    superposing a main chain of the visualized second steric structure and a main chain of the visualized first steric structure to compare the data of the second steric structure with the data of the first steric structure.

4. A non-transitory computer-readable recording medium having stored therein a program that causes a computer to execute a process, the process comprising:
    calculating a second steric structure of the peptide molecule by using data of a first steric structure of the peptide molecule, the first steric structure being a steric structure of the peptide molecule in a complex structure of a target molecule and the peptide molecule, the second steric structure being a stable steric structure of the peptide molecule in a state where a steric configuration of a main chain of the peptide molecule in the first steric structure is fixed, wherein the calculating the second steric structure further includes performing a ground state search using an annealing method for an Ising model converted based on a restriction condition of a side chain of the peptide molecule to calculate a minimum energy of the Ising model and to reduce computational cost; and
    comparing data of the second steric structure with the data of the first steric structure in order to search for a side chain having a difference in steric configuration between the two steric structures.

5. The non-transitory computer-readable recording medium according to claim 4, the process further comprising:
visualizing the second steric structure and the first steric structure to compare the data of the second steric structure with the data of the first steric structure.

6. The non-transitory computer-readable recording medium according to claim 5, the process further comprising: superposing a main chain of the visualized second steric structure and a main chain of the visualized first steric structure to compare the data of the second steric structure with the data of the first steric structure.

7. An information processing apparatus, comprising:
a memory; and a processor coupled to the memory and the processor configured to:
calculate a second steric structure of the peptide molecule by using data of a first steric structure of the peptide molecule, the first steric structure being a steric structure of the peptide molecule in a complex structure of a target molecule and the peptide molecule, the second steric structure being a stable steric structure of the peptide molecule in a state where a steric configuration of a main chain of the peptide molecule in the first steric structure is fixed, wherein the calculate the second steric structure further includes perform a ground state search using an annealing method for an Ising model converted based on a restriction condition of a side chain of the peptide molecule to calculate a minimum energy of the Ising model and to reduce computational cost; and
compare data of the second steric structure with the data of the first steric structure in order to search for a side chain having a difference in steric configuration between the two steric structures.

8. The information processing apparatus according to claim 7, wherein the processor is further configured to: visualize the second steric structure and the first steric structure to compare the data of the second steric structure with the data of the first steric structure.

9. The information processing apparatus according to claim 8, wherein the processor is further configured to: superpose a main chain of the visualized second steric structure and a main chain of the visualized first steric structure to compare the data of the second steric structure with the data of the first steric structure.

* * * * *